United States Patent [19]

Bakar

[11] Patent Number: 4,666,517

[45] Date of Patent: May 19, 1987

[54] ANTIPLAQUE ORAL COMPOSITION

[75] Inventor: Shamsul Bakar, New Brunswick, N.J.

[73] Assignee: Colgate-Palmolive Co., New York, N.Y.

[21] Appl. No.: 870,598

[22] Filed: Jun. 4, 1986

[51] Int. Cl.[4] ............................ C09K 3/00; A61K 7/18
[52] U.S. Cl. ........................................ 106/35; 424/52; 424/54; 424/55; 514/724
[58] Field of Search ............... 424/52, 54, 55; 106/35; 514/724

[56] References Cited

U.S. PATENT DOCUMENTS

| | | | |
|---|---|---|---|
| 2,837,463 | 6/1958 | Fosdick et al. | 424/57 |
| 3,622,662 | 11/1971 | Roberts et al. | 424/54 |
| 3,984,537 | 10/1976 | Harrison et al. | 424/54 |
| 3,989,814 | 11/1976 | Cordon et al. | 424/57 |
| 4,522,806 | 6/1985 | Muhlemann et al. | 424/52 |

OTHER PUBLICATIONS

Chem. Abst. vol. 93:161,851p, Kato.

*Primary Examiner*—Theodore Morris
*Attorney, Agent, or Firm*—Robert L. Stone; Murray M. Grill; Herbert S. Sylvester

[57] ABSTRACT

An oral composition such as a mouthwash, toothpaste, gel, toothpowder, tablet, lozenge, and the like comprising a synergistic combination of tridecanol-1 and hexetidine which inhibits the formation of dental plaque.

15 Claims, No Drawings

ANTIPLAQUE ORAL COMPOSITION

FIELD OF THE INVENTION

This invention relates to a novel antiplaque and antigingivitis oral composition containing the synergistic antibacterial combination of tridecanol-1 and hexetidine in the ratio of 1:1 to 5:1 of hexitidine:tridecanol-1 which also improves taste, i.e. reduces or eliminates the bitter taste of hexitidine.

BACKGROUND OF THE INVENTION

Hexetidine, which is an amino-hexahydro-pyrimidine derivative, is a broad-spectrum antibacterial, and has been formulated in a number of products including mouthrinses (Oraldene, Sterisil) and dentifrices (Mentadent-P). U.S. Pat. No. 2,837,463 discloses therapeutic compostions, including mouthwashes and dentifrices, containing said hexahydropyrimidine antibacterial compounds. British Pat. No. 771,768 also discloses dental therapeutic compositions containing a 5-methyl-5-amino-hexahydropyrimidine compound, said dental compositions including pastes, powders, liquids chewing gums, tablets, lozenges and troches.

The 5-aminohexahydropyrimidines and a process for their preparation is disclosed in U.S. Pat. No. 2,387,043 which is incorporated herein by reference.

U.S. Pat. No. 4,522,806, European Patent Application No. 049,830 and British Pat. No. 2,084,870 disclose oral compositions containing hexetidine and zinc salts for the synergistic inhibition of dental plaque without staining the teeth.

The use of hexetidine (5-amino-1,3-bis(2-ethylhexyl)-5-methyl-hexahydropyrimidine) as an optical antibacterial additive in oral compositions is known in the prior art as disclosed in U.S. Pat. Nos. 3,622,662; 3,984,537; 3,989,814; and in British Pat. Nos. 1,533,634 and 1,461,896.

However, the prior art does not disclose an antiplaque and anti-gingivitis oral product containing the synergistic antibacterial combination of hexetidine and tridecanol-1.

SUMMARY OF THE INVENTION

It has now been found that tridecanol-1 forms a synergistic combination with hexetidine, which can be used to formulate an oral care product as an effective remedy for plaque and gingivitis.

Accordingly, a primary object of present invention is to provide a novel oral antiplaque and antigingivitis composition based on the combination of hexetidine and tridecanol-1.

Another object of present invention is to increase the antibacterial activity of hexetidine.

Still another object of present invention is to improve the taste of oral products containing hexetidine.

Another object of present invention is to reduce or eliminate possible side effects, such as staining of teeth and a bitter taste, by using low levels of hexetidine in the oral product.

Additional objects, advantages and novel features of the invention will be set forth in part in the description which follows, and in part will become apparent to those skilled in the art upon examination of the following or may be learned by practice of the invention. The objects and advantages of the invention may be realized and attached by means of the instrumentalities and combinations particularly pointed out in the appended claims.

To achieve the foregoing and other objects and in accordance with the present invention as embodied and broadly described herein, the novel antiplaque and antigingivitis oral composition of this invention comprises an effective antibacterial amount of the synergistic combination of hexetidine and tridecanol-1 in the ratio of 1:1 to 5:1 of hexetidine:tridecanol-1 in a dental vehicle.

More specifically, present invention relates to an antiplaque and antigingivitis oral composition of improved taste, comprising the synergistic combination of low levels of hexetidine of about 0.075–0.5% by weight, and tridecanol-1 as the antibacterial agents, in the weight ratio of 1:1 to 5:1 of hexetidine:tridecanol-1, said composition having an acid pH up to 6 and preferably about 5–6.

Hexetidine is a broad-spectrum, water-insoluble antibacterial, having the chemical formula

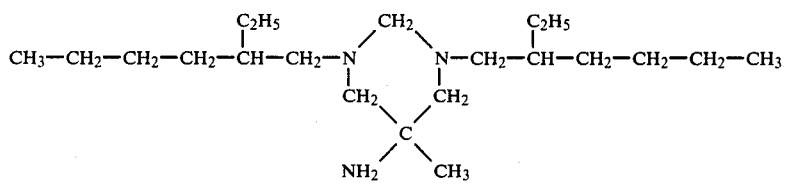

5-amino-1,3-bis(2-ethylhexyl)-5-methyl-hexahydropyrimidine. It has been used as an antibacterial agent in antiplaque and antigingivitis oral compositions as previously discussed. However hexetidine is a bitter-tasting chemical, thereby limiting its use to low levels in order to minimize its bitter taste, which in turn limits its therapeutic activity.

It has unexpectedly been found that tridecanol-1, a linear aliphatic alcohol ($C_{13}H_{27}OH$), forms a synergistic combination with hexetidine when tested against Strep. mutans, the bacteria found in plaque. Tridecanol-1 has been shown in a MIC test against S. mutans to be synergistic with the antibiotic gentamycin (IADR, Dallas, 1984, Abstract #138). Table I gives the MIC (minimum inhibitory concentration) results with Strep. mutans.

All the active ingredients (AI) are in water/alcohol/propylene glycol mixtures.

TABLE I

| Active Ingredient | ppm | Ratio | MIC, ppm | FIC Index* |
|---|---|---|---|---|
| Hexetidine/zinc++ | 150/150 | 1:1 | .12/.12 | 0.20* |
| Hexetidine/tridecanol-1 | 150/150 | 1:1 | .12/.12 | 0.25* |
| Hexetidine/tridecanol-1 | 150/750 | 1:5 | .24/1.2 | 0.92 |
| Hexetidine/tridecanol-1 | 150/30 | 5:1 | .12/.024 | 0.21* |
| Hexetidine | 750 | — | .60 | — |
| Zinc++ | 750 | — | 40.00 | — |
| Tridecanol-1 | 750 | — | 2.30 | — |

*If the FIC index ≦ 0.5, the combination is synergistic.

The lower MIC value is indicative of greater antibacterial activity. The FIC (Fractional Inhibitory Concentration), which is an indicator of synergism, has been calculated from the MIC data for each ratio.

The MIC results show that a 1:1 ratio and a 5:1 ratio of hexetidine:tridecanol-1 is a synergistic combination, whereas 1:5 ratio of hexetidine/tridecanol-1 is not synergistic, clearly showing the criticality of using a 1:1 to 5:1 ratio of hexetidine/tridecanol-1 in the present antiplaque compositions. This table also shows that the antimicrobial activity of the combination is not the sum total of the individual component's antibacterial activity, but is a synergistically more effective antibacterial agent at lower concentrations. A minimum concentration of 0.60 ppm hexetidine alone is needed for total bacterial inhibition, and a minimum concentration of 2.3 ppm of tridecanol alone is required for total bacterial inhibition; whereas a concentration of 0.12 ppm hexetidine in combination with 0.024–0.12 ppm tridecanol effects total bacterial inhibition. This increase in the antibacterial activity of the hexetidine due to the presence of tridecanol reduces the amount necessary to produce a therapeutic effect, and thus minimizes the bitter taste associated with the hexetidine. This MIC test also shows that hexetidine/tridecanol-1 is as synergistic as Hexetidine/Zn in a 1:1 ratio.

A similar set of experiments done concurrently with benzethonium chloride (BTC) shows that BTC/tridecanol-1(TDL) is not synergistic in any ratio as shown in Table II.

TABLE II

| AI (ppm) | AI (Ratio) | MIC ppm | FIC Index |
|---|---|---|---|
| BTC/Zn++ (150/150) | 1:1 | .47/.47 | .80 |
| BTC/TCL (150/150) | 1:1 | .47/.47 | .99 |
| BTC/TDL (150/150) | 1:5 | 1.20/.24 | 2.10 |
| BTC/TDL (150/30) | 5:1 | 0.47/.09 | .82 |

Accordingly, synergism of antibacterial activity of an antibacterial compound with tridecanol-1 is not predictable. It is specific to the particular antibacterial compound, hexetidine, used in present invention, in the formulation of an oral care product as an effective remedy for plaque and gingivitis.

The oral formulation in accordance with present invention may be in the form of a liquid such as a mouthwash or rinse, wherein the vehicle is typically a water-alcohol mixture containing a nonionic surfactant such as polyoxyethylene (20) sorbitan mono-isostearate or polyoxyethylene (40) sorbitan diisostearate and a humectant such as glycerin, propylene glycol and polyethylene glycol. The water is the major ingredient and constitutes about 65–80% by weight, with the alcohol constituting about 10–15% by weight of the composition. The humectant constitutes about 10–20% by weight, and the nonionic surfactant constitutes about 0.5–1% by weight of the composition. The pH of said liquid formulations is about 5–6.

The oral preparation may also be in the form of a dentifrice containing a dental polishing agent, such as a toothpaste, dental cream or a gel, wherein the liquid vehicle may comprise water, typically in an amount of about 10–90% by weight of the composition. Polyethylene glycol, propylene glycol, glycerin or mixtures thereof may also be present as humectants or binders in amounts of about 20–25% by weight. Particularly advantageous liquid ingredients comprise mixtures of water with polyethylene glycol or glycerin and propylene glycol. A gelling agent (thickening agent) including natural or synthetic gums such as sodium carboxymethylcellulose, hydroxyethyl cellulose, methyl cellulose and the like may be used, in the range of about 0.5–5% by weight. The preferred gelling agent is hydroxyethyl cellulose. In a toothpaste, dental cream or gel, the liquids and solids are proportioned to form a creamy or gelled mass which is extrudable from a pressurized container or from a collapsible tube.

The toothpaste or gel may also contain a surface active agent which may be an anionic, nonionic or zwitterionic detergent, in amounts of 0.05–5% by weight.

Suitable anionic detergents are water-soluble salts of higher fatty acid monoglyceride monosulphates, such as the sodium salt of the monosulphated monoglyceride of hydrogenated coconut oil fatty acids; higher alkyl sulphates, such as sodium lauryl sulphate; alkyl aryl sulphonates, such as sodium dodecyl benzene sulphonate; higher alkyl sulphoacetates; higher fatty acid esters of 1,2-dihydroxy propane sulphonates; and substantially saturated higher alkphatic acyl amides of lower aliphatic amino carboxylic acids such as those having 12 to 16 carbons in the fatty acid, alkyl or acyl radicals. Examples of the last mentioned amides are N-lauroyl sarcosine, and the sodium, potassium, and ethanolamide salts of N-lauroyl, N-myristyl or N-palmitoyl sarcosine.

Nonionic surface active agents include condensates of sorbitan monostearate with approximately 20–60 moles of ethylene oxides (e.g. "Tweens"); condensates of ethylene oxide with propylene oxide condensates of propylene glycol ("Pluronics"); condensates of higher fatty alcohols or ethers with ethylene oxide; condensates of alkyl thiophenols with 10 to 15 ethylene oxide units; and ethylene oxide addends of monoesters of hexahydric alcohols and inner esters thereof such as sorbitan monolaurate, sorbitol monooleate, mannitan monopalmitate, and sorbitan monoisostearate.

Zwitterionic surface active agents include the betaines and sulfobetaines. Typical alkyl dimethyl betaines include decyl betaine or 2-(N-decyl-N,N-dimethylammonio)acetate, coco betaine, myristyl betaine, palmityl betaine, lauryl betaine, cetyl betaine, stearyl betaine, etc. The amidobetaines similarly include cocoamidoethyl betaine, cocoamidopropyl betaine, lauramidopropyl betaine and the like. These sulfobetaines are similar in structure to the betaines, but have a sulfonate group in place of the carboxylate group, and include alkylsulfobetaines, alkylamidosulfobetaines and alkylaminosulfobetaines.

A toothpowder, toothpaste or gel contains conventional water-insoluble dental polishing material, which is compatible with the formulation. The polishing agent may be the sole carrier material as in a toothpowder consituting about 70–99% by weight of the toothpowder; or be present in a toothpaste or gel in amounts of about 20–75% by weight of the oral composition. Suitable polishing agents include hydrated alumina, calcined alumina, silica, dihydrated dicalcium phosphate, sodium or potassium metaphosphate, tricalcium phosphate and other phosphate salts, calcium carbonate, aluminum silicate, zirconium silicates, plastics such as polymethacrylate, bentonite and mixtures thereof. Preferred polishing materials include calcined alumina, hydrated alumina and silica.

Various other materials may be incorporated in the oral preparations of the invention, including coloring or whitening agents, preservatives, perfumes, a fluorine-providing compound such as sodium fluoride, potassium fluoride, sodium monofluorophosphate and the like, flavoring agents and sweeteners and mixtures thereof, in amounts which do not adversely affect the antibacterial properties and characteristics of present novel oral composition.

The oral composition of this invention is prepared by conventional methods of making mouthwashes, toothpastes, dental creams and gels. More specifically, a toothpaste or dental gel may be prepared by dispersing a gelling agent in a liquid (humectant and/or water), adding to and mixing with said dispersion an aqueous solution of water-soluble ingredients such as fluorides, saccharin and the like, followed by the addition with mixing of the polishing agent, and lastly admixing the surfactant, the antibacterial synergistic combination and flavor, and tubing or otherwise packaging the final composition.

In the preparation of tooth powders, it is usually sufficient to admix mechanically, e.g., by milling, the various solid ingredients in appropriate quantities and particle sizes.

The mouthwash is prepared by dissolving hexetidine, tridecanol-1, flavor, humectant (such as propylene glycol, etc.) and the surfactant in alcohol. The nonionic surfactants also function as solubilizers. The water-soluble ingredients such as sodium saccharin, fluoride, color, etc. are dissolved in deionized water. The alcoholic and aqueous solutions are mixed together to form the mouthwash.

In the practice of this invention, to promote oral hygiene, the oral composition according to this invention is applied regularly to dental enamel by brushing the teeth and/or rinsing the oral cavity for 30–90 seconds at least once a day.

DETAILED DESCRIPTION OF THE INVENTION

The following examples are merely illustrative by the invention, but it is understood that the invention is not limited thereto. All amounts of various ingredients are by weight unless otherwise specified.

EXAMPLES I AND II

| | Mouthrinse | |
|---|---|---|
| | % | |
| Ingredients | I | II |
| Hexetidine | 0.075 | 0.075 |
| Tridecanol-1 | 0.075 | 0.015 |
| Ethanol (95%) | 15.000 | 15.000 |
| Propylene glycol | 20.000 | 20.000 |
| Solubilizer (POE-20)' | 2.000 | 2.000 |
| Flavor | 0.300 | 0.300 |
| Sodium saccharin | 0.040 | 0.040 |
| Sodium fluoride | 0.050 | 0.050 |
| Color (1.0% solution) | 0.050 | 0.050 |
| Water, | q.s. to 100.000 | q.s. to 100.000 |

'Polyoxyethylene (20) sorbitan monoisostearate

The hexetidine/tridecanol ratios in Example I and II and 1:1 and 5:1 respectively. These ratios are synergistic.

The mouthrinses are made by dissolving hexetidine, tridecanol, propylene glycol, solubilizer and flavor in ethanol and then adding to it an aqueous solution of sodium saccharin, sodium fluoride and color. The pH is adjusted to 6.0 with 1.0N hydrochloric acid.

EXAMPLES III AND IV

| | Toothpaste Dental Cream | |
|---|---|---|
| | % | |
| Ingredients | III | IV |
| Hexetidine | 0.50 | 0.50 |
| Tridecanol-1 | 0.50 | 0.10 |
| Flavor | 1.00 | 1.00 |
| Emulsifier[1] | 4.50 | 4.50 |
| Carbowax 600[2] | 20.00 | 20.00 |
| Hydroxyethyl cellulose | 1.30 | 1.30 |
| Sodium saccharin | 0.40 | 0.40 |
| Sodium fluoride | 0.24 | 0.24 |
| Hydrated alumina | 42.00 | 42.00 |
| Calcined alumina | 10.00 | 10.00 |
| Water, deionized, | q.s. to 100.00 | q.s. to 100.00 |

[1]Cocoamidopropyl betaine (30% A.I.) (1-alkylamino-3 dimethylammonio-propane-3-carboxymethyl-betaine)
[2]Polyethylene glycol, mol. weight 600

The hexetidine/tridecanol ratios in Example III and IV are 1:1 and 5:1 respectively. These dentifrices are made by adding an aqueous solution of sodium saccharin and sodium fluoride to the dispersion of hydroxyethyl cellulose in polyethylene glycol and is mixed for about half an hour. This mixture is added to a mixture of hydrated alumina and calcined alumina, and mixed for about 20 minutes under vacuum. The emulsifier, flavor, hexetidine and tridecanol are added thereto and mixed for another 10 minutes under vacuum. The pH of the final product is about 6.0.

EXAMPLES V AND VI

| | Toothpaste Gel | |
|---|---|---|
| | % | |
| | V | VI |
| Hexetidine | 0.50 | 0.50 |
| Tridecanol-1 | 0.50 | 0.10 |
| Flavor | 1.00 | 1.00 |
| Emulsifier[1] | 4.50 | 4.50 |
| Glycerine | 25.00 | 25.00 |
| Hydroxyethyl cellulose | 1.20 | 1.20 |
| Sodium saccharin | 0.30 | 0.30 |
| MFP (Sod. monofluoro phosphate) | 0.76 | 0.76 |
| Propylene glycol | 10.00 | 10.00 |
| ZEO 49 B (Hydrated Silica) | 20.00 | 20.00 |
| Syloid 244[2] | 5.00 | 5.00 |
| Titanium dioxide | 0.50 | 0.50 |
| Water, deionized, | q.s. to 100.00 | q.s. to 100.00 |

[1]Cocoamidopropyl Betaine (Goldschmidt Chem. Corp.)
[2]Micron sized amorphous silica (Davidson Chem. Div.).

Examples V and VI are similarly prepared in accordance with the method used in Examples III and IV.

Variations in the above formulations may be made. For example, other polishing agents may be substituted for the specific polishing agents in the examples. Similarly other surfactants may be substituted for the specific surfactants in the Examples.

It is understood that the foregoing detailed description is given merely by way of illustration and that variations may be made therein without departing from the spirit of the inventor. The "Abstract given above is merely for the convenience of technical searchers and is not to be given any weight with respect to the scope of the invention.

What is claimed is:

1. An antiplaque oral composition with improved taste, comprising an effective antibacterial amount of the synergistic combination of hexetidine and tridecanol-1, in the ratio of 1:1 to 5:1 of hexetidine:tridecanol which inhibits the formation of dental plaque, in a dental vehicle having an acid pH of about 5-6.

2. The oral composition according to claim 1, wherein the hexetidine constitutes about 0.075-0.5% by weight of the composition.

3. The oral composition according to claim 1, in the form of a liquid mouth rinse, wherein the vehicle is a water and alcohol mixture.

4. The mouthrinse according to claim 3, wherein the vehicle contains a nonionic surfactant and a humectant.

5. The oral composition according to claim 1, in the form of a dentifrice containing about 20-75% by weight of a dental polishing agent and a liquid vehicle.

6. The dentifrice according to claim 5, wherein the liquid vehicle contains a mixture of about 10-90% water and about 20-25% humectants.

7. The dentifrice according to claim 5, wherein the dental polishing agent is a mixture of hydrated alumina and calcined alumina.

8. The dentifrice according to claim 5, wherein the dental polishing agent is silica.

9. The oral composition according to claim 4 or claim 6, wherein the humectant is selected from the group consisting of propylene glycol, polyethylene glycol, glycerin and mixtures thereof.

10. The dentifrice according to claim 6, wherein the vehicle contains a gelling agent and a surfactant selected from the group consisting of anionic, nonionic, zwitterionic detergents and mixtures thereof.

11. The mouthrinse according to claim 4 wherein the nonionic surfactant is polyoxyethylene (20) sorbitan monostearate.

12. The dentifrice according to claim 10, wherein the gelling agent is hydroxyethyl cellulose.

13. The dentifrice according to claim 10, wherein the surfactant is cocoamidopropyl betaine.

14. The oral composition according to claim 1, containing a fluorine-providing compound.

15. The oral composition according to claim 14 wherein said fluorine-providing compound is selected from the group consisting of sodium fluoride and sodium monofluorophosphate.

* * * * *